United States Patent [19]
Koashi et al.

[11] Patent Number: 5,533,509
[45] Date of Patent: Jul. 9, 1996

[54] METHOD AND APPARATUS FOR NON-INVASIVE MEASUREMENT OF BLOOD SUGAR LEVEL

[75] Inventors: Katsue Koashi, Toyonaka; Shigeo Minami, Ashiya, both of Japan

[73] Assignee: Kurashiki Boseki Kabushiki Kaisha, Okayama, Japan

[21] Appl. No.: 411,631

[22] PCT Filed: Aug. 12, 1993

[86] PCT No.: PCT/JP93/01140

§ 371 Date: Apr. 10, 1995

§ 102(e) Date: Apr. 10, 1995

[87] PCT Pub. No.: WO95/05120

PCT Pub. Date: Feb. 23, 1995

[51] Int. Cl.$^6$ .................................................. A61B 5/00
[52] U.S. Cl. ..................... 128/633; 128/665; 356/41
[58] Field of Search ......................... 128/633, 664–6; 351/41

[56] References Cited

U.S. PATENT DOCUMENTS

| | | |
|---|---|---|
| 3,638,640 | 2/1972 | Shaw . |
| 3,958,560 | 5/1976 | March . |
| 4,169,676 | 10/1979 | Kaiser . |
| 4,883,953 | 11/1989 | Koashi et al. . |
| 5,183,042 | 2/1993 | Harjunmaa et al. ............ 128/633 |
| 5,372,135 | 12/1994 | Mendelson et al. ............ 128/633 |
| 5,377,674 | 1/1995 | Kuestner ........................ 128/633 |
| 5,398,681 | 3/1995 | Kuperschmidt ................ 128/633 |

FOREIGN PATENT DOCUMENTS

| | | |
|---|---|---|
| 1-131436 | 5/1989 | Japan . |
| 612271 | 7/1979 | Switzerland . |
| 2033575 | 5/1980 | United Kingdom . |
| 2075668 | 11/1981 | United Kingdom . |
| WO81/00622 | 3/1981 | WIPO . |

OTHER PUBLICATIONS

Clinical Chemistry, vol. 25, No. 9 (1979), T. C. O'Haver, "Potential Clinical Applications of Derivative and Wavelength–Mofulation Spectrometry".

Nikkei Electronics, No. 423, (1987), K. Kobayashi and I. Mito.

Primary Examiner—Angela D. Sykes
Assistant Examiner—Robert L. Nasser, Jr.
Attorney, Agent, or Firm—Wenderoth, Lind & Ponack

[57] ABSTRACT

To intensity-modulate laser light periodically wavelength-modulated by and emitted from a wavelength-variable semiconductor laser 11. To separate the laser light into optical paths 13a, 13b with a beam splitter 14 to irradiate an examined location 17 for assessing blood sugar through path 13a. To detect the intensity of transmitted or reflected light from examined location 17 with a first detector 21 and the intensity of laser light passing through path 13b with a second detector 22 to detect the ratio of the former intensity to the latter intensity with a logarithmic ratio amplifier 25. To detect the rate of change in the ratio with respect to the change in wavelength of the wavelength modulation with a lock-in amplifier 26 to obtain a derivative spectral signal of the absorption spectrum of glucose. An arithmetic processor 27 detects blood sugar in the examined location from the derivative spectrum.

5 Claims, 13 Drawing Sheets

METHOD AND APPARATUS FOR NON-INVASIVE MEASUREMENT OF BLOOD SUGAR LEVEL

BACKGROUND OF THE INVENTION

1. Field of the Invention

The present invention relates to a method and apparatus for non-invasively measuring a blood sugar level on an in vivo and in situ basis using spectroscopic techniques. More specifically, the invention relates to a method and apparatus for non-invasively measuring the concentration of glucose in the blood stream or tissue of a patient suspected of suffering from diabetes based on a combination of wavelength modulation and intensity modulation of light.

2. Description of the Related Art

Various methods and apparatus for measuring the concentration of glucose in vitro and in vivo using spectroscopic techniques have been proposed.

For example, International application No. WO 81/00,622 discloses a method and apparatus for measuring the absorption of infrared light by glucose in body fluid using $CO_2$ laser light as an irradiation light source. The method and apparatus measure the absorption spectra of serum and urine by transmittance and reflectance, i.e.—back scattering effects, at different wavelengths $\lambda_1$ and $\lambda_2$. Here, $\lambda_2$ is a characteristic absorption wavelength of the substance to be measured, e.g. glucose, and $\lambda_1$ is a wavelength at which absorption is independent of the concentration of the substance to be measured. The measurements are obtained by calculating the ratio of the absorbance at $\lambda_1$ to the absorbance at $\lambda_2$. The absorption band of the substance to be measured is between 940 $cm^{-1}$: and 950 $cm^{-1}$; ie. between 10.64 and 10.54 μm for wavelength $\lambda_1$, and the absorption band is between 1090 $cm^{-1}$; and 1095 $cm^{-1}$; i.e.—between 9.17 μm and 9.13 μm for wavelength $\lambda_2$.

U.S. Pat. No. 4,169,676 discloses an non-invasive examining method for detecting biological substances through skin using an attenuated-total-reflectance (ATR) prism. The method attaches the wave guide (ATR prism) directly to the surface of a sample under examination (e.g. a lip or tongue) and guides in infrared light. The refractive index of the wave guide is greater than that of the sample medium, ie. an optically thin layer of the surface, and the infrared light is made to pass through the prism along the total-reflection path. The infrared light interacts with the thin layer of the surface, and the interaction is related to the frustrated attenuation component of the light at the reflecting part (see Hormone & Metabolic Res. Suppl. Ser. (1979) pp. 30– 35). If infrared light of a wavelength related to the absorption of glucose is used, then the light passing through the prism is attenuated depending on the concentration of glucose in the optically thin layer of the surface. Therefore, the attenuated quantity is detected and processed into data on the glucose concentration.

U.S. Pat. No. 3,958,560 discloses a non-invasive detection apparatus that detects glucose in a patient's eye. Specifically, the apparatus of this U.S. patent is a sensor apparatus in shape of a contact lens comprising a light source that applies infrared light to one side of cornea and a detector that detects the transmitted light on the opposite side. When infrared light is applied to a measured location, the infrared light passes through the cornea and the aqueous humor and reaches the detector. The detector converts the quantity of transmitted light into an electric signal and provides it to a remote receiver. Then the reader of the receiver outputs the concentration of glucose in the patient's eye as a function of the individual change of quantity in the applied infrared light passing through the eye.

British Pat. application No. 2,035,557 discloses a detecting apparatus for assessing substances near the blood stream of a patient such as $CO_2$, oxygen, or glucose. The detecting apparatus comprises an optical source and an optical receiving means that detects attenuated light back-scattered or reflected from inside a patient's body, i.e.—from the hypoderma, and uses ultraviolet or infrared light as the irradiation light.

On the other hand, there are following apparatus that measure or monitor the flow of blood and organism-activating parameters or components such as oxygenated hemoglobin and reduced oxyhemoglobin.

U.S. Pat. No. 3,638,640 discloses a method and apparatus for measuring oxygen and other substances in blood and the tissue. The U.S. Pat. apparatus comprises an irradiation light source and a detector placed on a patient's body. If the detector is placed on an ear, then the intensity of light passing through the ear is measured, and if the detector is placed on a forehead, then the intensity of light reflected after passing through blood and the hypoderma is measured. The wavelengths between red light and near-infrared light are used as the irradiation light, i.e.—660 nm, 715 nm, and 805 nm. The number of wavelengths used at the same time is 1 plus the number of wavelengths characteristic of substances existing in the examined location. Signals obtained by detecting from absorption at various wavelengths are processed by an electric circuit, so that quantitative data concerning the concentration of the substance to be measured is obtained without being influenced by the fluctuation of measuring conditions such as the fluctuation of the detector, the deviation of the intensity, the direction and angle of irradiation, and the fluctuation of the flow of blood in the examined location.

Further, British pat. No. 2,075,668 discloses a spectrophotometric apparatus for measuring and monitoring metabolic functions of an organism such as changes in oxidation and reduction of hemoglobins and cytochromes or changes in the blood flow in an organ such as the brain, heart, lever on an in vivo and in situ basis. The apparatus uses an irradiation light of wavelengths between 700 nm and 1,300 nm, which effectively penetrates several mm deep under skin.

FIG. 14 of the British patent application illustrates an apparatus for measuring reflectance comprising a wave guide (optical fiber tube) to be abutted to an organism and a light source. The wave guide is abutted to an organism so that irradiation light is applied to the surface of skin in an oblique direction, and the oriented irradiation light is made to penetrate into the body through skin and to be reflected or back-scattered from the tissue at a distance apart from the light source. Some of the light energy is absorbed and the rest is incident on a first detector placed on skin and apart from the light source. Also a second detector is placed and detects a backward-radiated reference signal. The analytical signal from the first detector and the reference signal from the second detector are output into an arithmetic operation circuit, and the data of analytical information is obtained as the output of the arithmetic operation circuit.

In measurement of the concentration of glucose and the like described above, the quality of the spectroscopic data obtained by a near-infrared spectrometer is determined by the performance of hardware constituting the near-infrared spectrometer. At present, the signal to noise ratio S/N of the best performance is approximately on the order between $10^5$ to $10^6$. On the other hand, for example, the prior methods of measuring the absolute intensity of the spectrum requires $10^5$ to $10^6$ order as the S/N ratio of the spectral signal to measure 100 mg/dL, which is the physiological concentration of glucose in blood, with spectroscopically practical precision, so that the measurement must be done near the maximum precision limit attainable by the spectrometer.

Therefore, methods of measuring the concentrations of sugar and glucose and the like using spectroscopic techniques have less sensitivity, precision and accuracy than chemical analysis that analyzes the concentrations of these substances using reagents, and a near-infrared spectrometer of high performance having a high S/N ratio is made with complex construction at great cost. Thus, if a variation of glucose concentration from the physiological concentration of glucose, 100 mg/dL, can be measured with the precision of 2 to 3 digits by a reference method, instead of simply measuring the absolute intensity of a spectrum, then we can find how much the blood sugar of a patient deviates from a normative value, so that the measurement can be favorably used for controlling the blood sugar of the patient.

SUMMARY OF THE INVENTION

The object of the present invention is therefore to provide a method of measuring blood sugar that easily and non-invasively measures the variation of the blood sugar of a patient suspected of suffering from diabetes from a normative value independent of the patient's individual differences using a modulation means that combines wavelength modulation with intensity modulation.

Another object of the present invention is to provide a compact and inexpensive apparatus for measuring blood sugar that easily and non-invasively measures the variation of the blood sugar of a patient suspected of suffering from diabetes from a normative value independent of the patient's individual differences with a simple construction comprising a wavelength modulation means and an intensity modulation means.

In order to achieve the aforementioned objectives, the present invention intensity-modulates light with several intensities as well as wavelength-modulating, applies the modulated light to an examined location for assessing blood sugar, detects, for each intensity-modulated light, the intensity of the transmitted and reflected light from a portion to be examined and the intensity of the incident light onto the portion to be examined, detects the ratio of the two intensities, detects the rate of change in the ratio with respect to the change in the wavelength due to the above wavelength-modulation, extracts the derivative spectrum of the absorption spectrum of glucose in that portion, and detects the blood sugar of that portion based on these derivative spectra for all modulating intensities of light.

In this way, light which is intensity-modulated as well as being wavelength-modulated with a small modulation width $\Delta\lambda$ around a considered wavelength is applied to the examined portion, and the depth of penetration into skin is varied by the intensity modulation of the incident light on the examined location, so that information concerning the concentration of glucose in the examined portion, where body fluid including blood components exists, is extracted, and determination of glucose in the examined location is performed based on the derivative spectra of the absorption spectra. Therefore, the concentration of glucose is easily and securely detected independently of individual differences of the patient.

The above derivative spectra are preferably accumulated and averaged corresponding to the iteration of the above wavelength modulation. If, in this way, the derivative spectra are accumulated and averaged, then the noise component is reduced in proportion to the square root of the number of accumulation, so that the signal to noise ratio S/N is improved.

The present invention provides an apparatus comprising a wavelength-modulated light generator that generates wavelength-modulated light, an intensity modulator that intensity-modulates the wavelength-modulated light output from the wavelength-modulated light generator into several intensities, a beam splitter that separates the optical path of the wavelength-modulated and intensity modulated light emitted from the intensity modulator, an optical collector that collects the light passing along one of the optical paths separated by the beam splitter, made incident on the examined location for assessing blood sugar, and being transmitted or reflected thereby, a first photo detector that detects the intensity of the light collected by the optical collector, a second photo detector that detects the intensity of the light passing along the other path separated by the beam splitter, a ratio detector that detects the ratio of the output of the first photo detector to the output of the second photo detector, a derivative spectral signal detector that reads a ratio signal output from the ratio detector, detects the rate of change in the ratio signal with respect to the change in wavelength due to the above wavelength modulation, and detects the derivative spectral signal of the absorption spectrum of glucose in the examined portion, an arithmetic means that calculates blood sugar in the examined portion for each intensity of the intensity-modulated light based on the derivative spectral signal detected by the derivative spectral signal detector.

The present invention wavelength-modulates light in the wavelength-modulated light generator and intensity-modulates the wavelength-modulated light to make it incident on the examined portion and detects the difference spectrum of the absorption spectrum of glucose, so that derivative data of high quality is obtained in real time without requiring computer processing. Further, the speed of iterative scanning is higher than an ordinary spectrometer, which scans a wide range of wavelengths, so that measured data on the concentration of glucose can be obtained by short-time photometry without being much influenced by a drift of the optical system.

The above wavelength-modulated light generator is preferably a wavelength-variable semiconductor laser. A semiconductor laser developed for use in optical fiber communications can be employed as the wavelength-variable semiconductor laser, so that the characteristics of a wavelength-variable semiconductor laser can be effectively utilized at its maximum performance, and the construction of the means for wavelength-modulating the measured light is extremely simplified. Therefore, the construction of the apparatus for non-invasive measurement of blood sugar becomes simple and compact.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

The preferred embodiments according to the present invention will be described below with reference to the appended drawings.

Items [1] and [2] below describe the derivative spectroscopy necessary for understanding the present invention and a method of wavelength modulation for obtaining derivative spectra. Furthermore, items [3], [4], and [5] respectively described the verification of determining glucose from the first derivative spectra, the choice of optimal wavelength, and the diffuse reflectance spectra of skin and intensity-modulation spectroscopy. Finally the configuration of an apparatus for non-invasive measurement of blood sugar in accordance with the present invention is described in item [6].

[1] Derivative spectroscopy

Wavelength modulation is generally used to obtain derivative spectra. The method of wavelength modulation is described in T. C. O'Haver, "Potential clinical applications of derivative and wavelength-modulation spectroscopy", (Clinical Chemistry, Vol 25, No. 9 (1979), pp. 1548–1553). The concept of wavelength-modulation spectroscopy is closely connected to the concept of derivative spectroscopy, and they are both based on the measurements of changes in intensity and absorbance with respect to a change in wavelength.

First, derivative spectroscopy is described. Derivative spectroscopy obtains the first or higher-order derivatives of the intensity or absorbance spectrum with respect to wavelength and plots the results. The purposes of the derivative spectroscopy are:

(a) the compensation and correction of the baseline shift, and (b) the effective increase in sensitivity to subtle changes in the shape of the spectral band.

Figure 1:
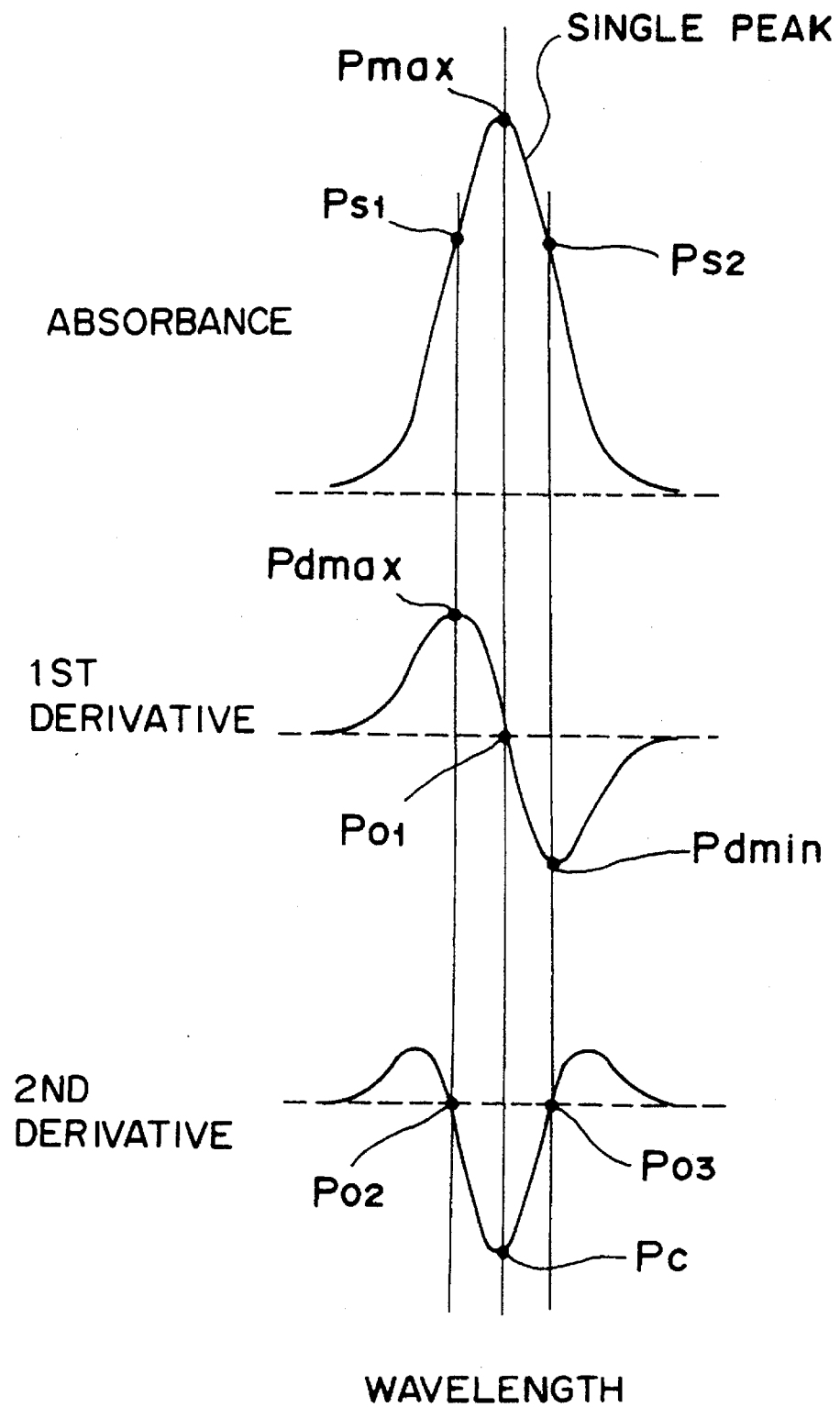
FIG. 1 shows a single peak spectrum, its first derivative spectrum, and its second derivative spectrum.

FIG. 1 shows a single peak spectrum and its first and second derivative spectra. The peak maximum point $P_{max}$ corresponds to the zero-crossing point $P_{01}$ of the first derivative and the central peak point $P_c$ of the second derivative. The peak maximum point $P_{dmax}$ and the peak minimum point $P_{dmin}$ of the second derivative respectively correspond to the maximum slope points $P_{s1}$ and $P_{s2}$ of the original spectrum and also respectively correspond to the zero-crossing points $P_{02}$ and $P_{03}$ of the second derivative.

There are several methods of obtaining derivative spectra as follows.

First, if the spectral data are digital values and can be processed by a computer, then the derivative spectra can be computed by numerical differentiation in software.

Secondly, the derivative spectra can be acquired in real time through time derivatives obtained by constant-speed scanning in hardware. This technique is based on the fact that if the wavelength scanning rate $d\lambda/dt$ is constant, then the derivative $dI/d\lambda$ of the intensity $I$ with respect to wavelength $\lambda$ is proportional to the derivative $dI/dt$ of the intensity $I$ with respect to time $t$, as is clear from the following (1). That is, by means of an electronic differentiator, the following equation (1) can be calculated.

$$dI/d\lambda = (dI/dt)/(d\lambda/dt) \quad (1)$$

Thirdly, derivative spectra can be obtained by a wavelength modulation described below.

Figure 2:
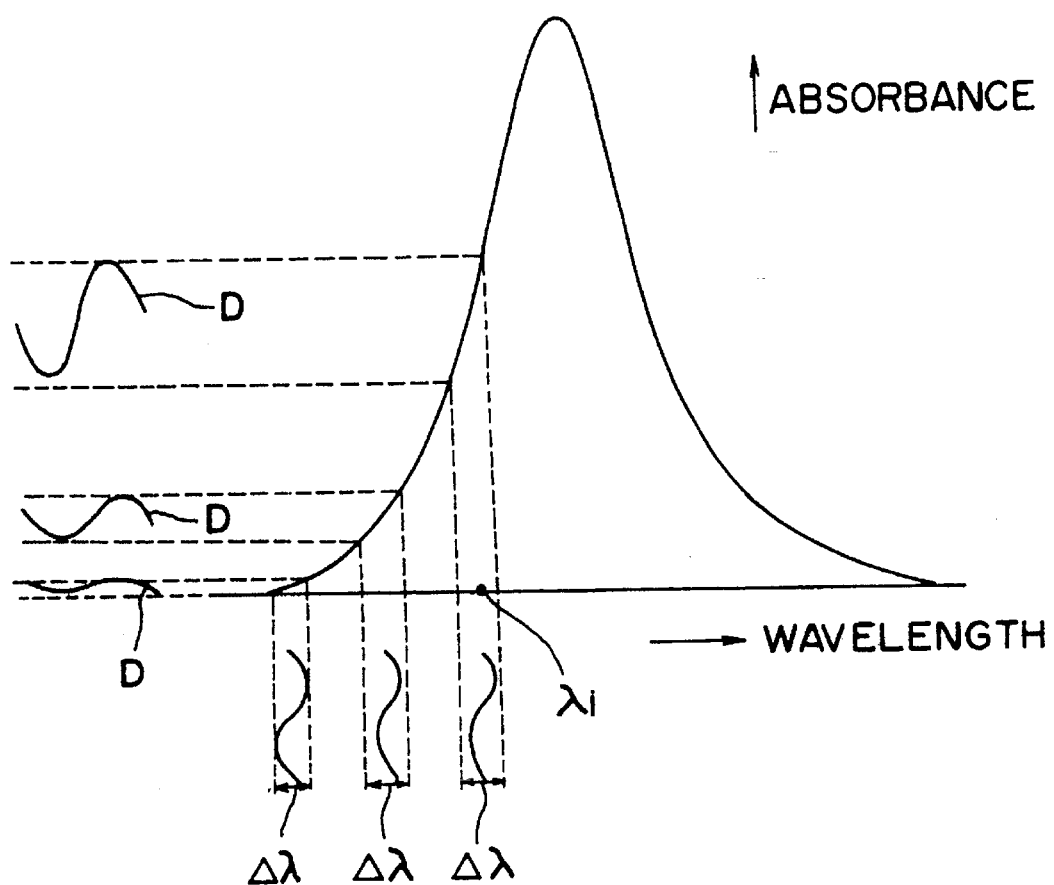
FIG. 2 shows the generation of a derivative spectrum by wavelength-modulation spectroscopy.

As shown in FIG. 2, a technique of wavelength modulation irradiates a sample with periodically modulated light having a narrow modulation width $\Delta\lambda$ around a particular wavelength $\lambda_i$ and detects the transmitted or reflected light with a detector. The ripple or the alternating-current component of the output signal from the detector is separated or electrically measured. If the modulation width $\Delta\lambda$ is sufficiently smaller than the bandwidth of the spectrum, then the alternating-current component of the optoelectronic signal at the modulation frequency generates an alternating-current signal, i.e.—a derivative spectrum D, which has an amplitude proportional to the slope of the spectrum within the modulation wavelength width.

There are several techniques for the wavelength modulation described above as follows:

(a) vibrating the slit, mirror, diffraction grating, or prism of a monochromator.

(b) inserting a vibrating mirror or rotary refracting mirror.

(c) using a wavelength-continuous-variable filter.

(d) vibrating or tilting a diffraction filter.

(e) vibrating a Fabry-Perot interferometer. Besides, (f) using a continuous-wavelength-variable semiconductor laser can be also considered.

The method of installing a reflective diffraction grating outside a semiconductor laser and controlling the angle of the diffraction grating to vary the oscillatory wavelength has been known. This method can vary the wavelength in a narrow spectral line width. If the variation is not necessarily continuous and if jumps between longitudinal modes are allowed, then the construction of the apparatus can be simplified.

If a single-mode filter that is synchronous with a tuning wavelength within a narrow bandwidth is added, then oscillation occurs at an arbitrarily set wavelength in a single mode. This apparatus is called a tunable semiconductor laser of the external resonance type.

Furthermore, a wavelength-variable semiconductor laser developed for use of coherent optical communications is described in Nikkei electronics, No. 423 (Jun. 15, 1987), pp. 149–161. In this article, semiconductor lasers that control wavelength with a tri-electrode construction based on the distributive Bragg-reflection laser of single mode are described. One of the semiconductor lasers continuously varies wavelength in a single longitudinal mode within a wavelength range of 3.1 nm. If the longitudinal mode is allowed to change in a middle, then the wavelength range is about 6 nm.

[2] Method of wavelength modulation for obtaining derivative spectra.

If, in wavelength modulation, the modulation width $\Delta\lambda (=\lambda_2-\lambda_1)$ is sufficiently less than the bandwidth of the spectrum, then the alternating-current component of the optoelectronic signal at the modulation frequency generates an alternating-current signal $\Delta I/\Delta\lambda$, i.e.—a derivative spectrum D expressed by the following (2), which has an amplitude proportional to the slope of the spectrum within the modulation wavelength width. The amplitude of the alternating-current signal can be obtained in real time by an appropriate electrical system.

$$D=\Delta I/\Delta\lambda=(I_2-I_1)/(\lambda_2-\lambda_1) \quad (2)$$

In general, the direct-current component is greater than the alternating-current component in measurement of a low concentration of glucose. Since the direct-current-component having such insignificant great values can be cut off, the dynamic range of the A-D converter used in an apparatus for the measurement of blood sugar described later can be efficiently used, and mathematical processing is performed thereafter at an advantage.

Wavelength modulation is performed by scanning periodically upward and downward within a narrow modulation width $\Delta\lambda$, so that the scanning can be repeated at a higher speed than by an ordinary spectrometer, which scans a wide range of wavelength. Therefore, the accumulation and averaging are easily performed. Since the noise component can be reduced in proportion to the square root of the number of accumulated measurements, the signal to noise ratio (S/N) can be improved by making the number of accumulated measurements large. Furthermore, short measurement times effectively suppress a drift of the optical system of the spectrometer.

The wavelength range in wavelength modulation is limited to a narrow $\Delta\lambda$, but derivative spectra of a high quality are obtained in real time without any computer processing. Therefore, wavelength modulation is suitable for a routine analysis of samples whose characteristics are already well known, for example, for quality control and clinical analysis.

On the other hand, if an original spectrum of digital values is processed by a numerical derivative operation, the numerical precision and quality of the intensity $I_i$ itself pose a problem.

The process of obtaining a derivative spectrum tends to enhance high-frequency noise in the original spectrum. If used improperly, the S/N ratio is greatly reduced by a derivative operation of a spectrum of low quality.

Further, in measurement of a sample of low absorption, unless the numerical precision or the number of significant digits of the intensity $I_i$ of an original spectrum is great, a significant change in the desired derivative spectrum can not be obtained. That is, the S/N ratio needs to be very large.

[3] The verification of determining glucose from first derivative spectra

If the spectral data have digital values, then their derivative spectra can be computed by numerical differentiation of the absorbance spectra. Therefore, we obtained the first derivative spectrum of an absorbance spectrum obtained by a Fourier-transform spectrometer by numerical differentiation to test the validity of the determination of glucose concentration by the wavelength modulation technique.

As samples, and we used pure water, aqueous solutions of glucose of 1,000 mg/dL, 3,000 mg/dL, and 5,000 mg/dL.

Since it is difficult to observe the differences among samples in detail in comparing the absorbance spectrum and the first derivative spectrum of each sample with that of each other sample, we calculated the differences between each sample and the standard pure water. That is, we calculated the difference absorbance spectrum and the difference of the first derivative spectrum of each sample to make the differences observable. The derivative operation was performed in the direction from longer wavelength to shorter wavelength.

Figure 3:
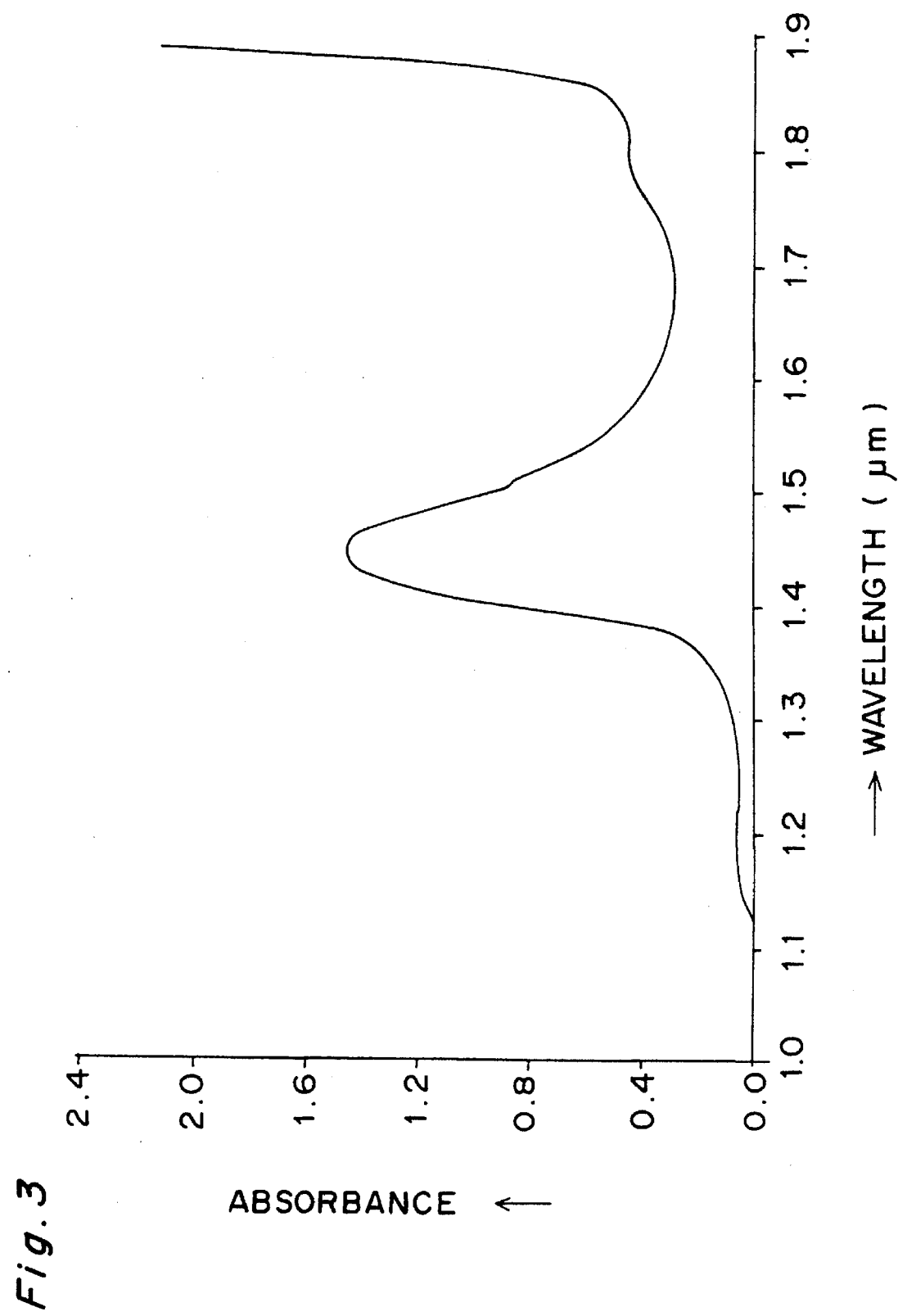
FIG. 3 shows an absorbance spectrum of an aqueous solution of glucose.
Figure 4:
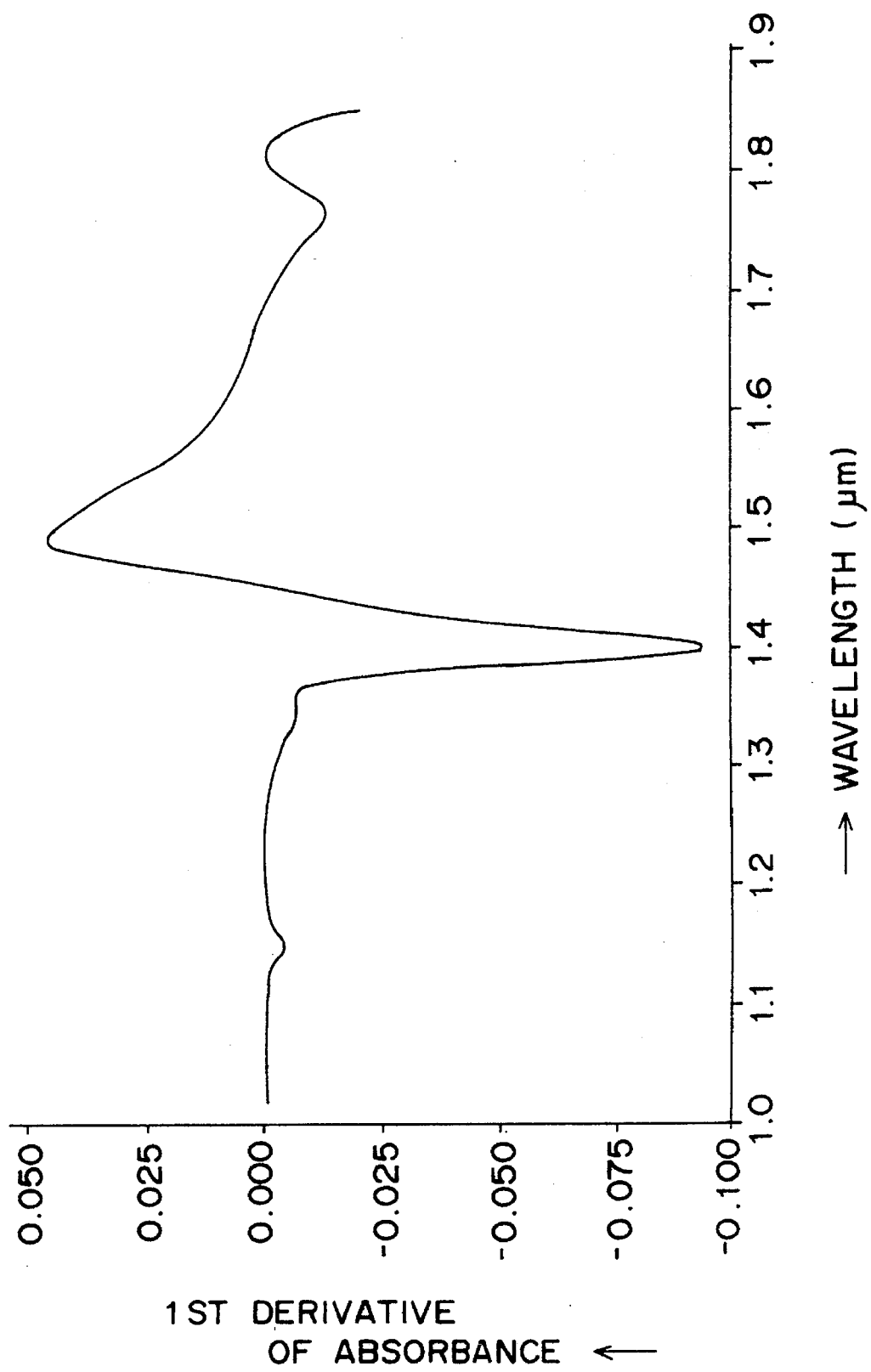
FIG. 4 shows the first derivative spectrum of FIG. 3.
Figure 5:
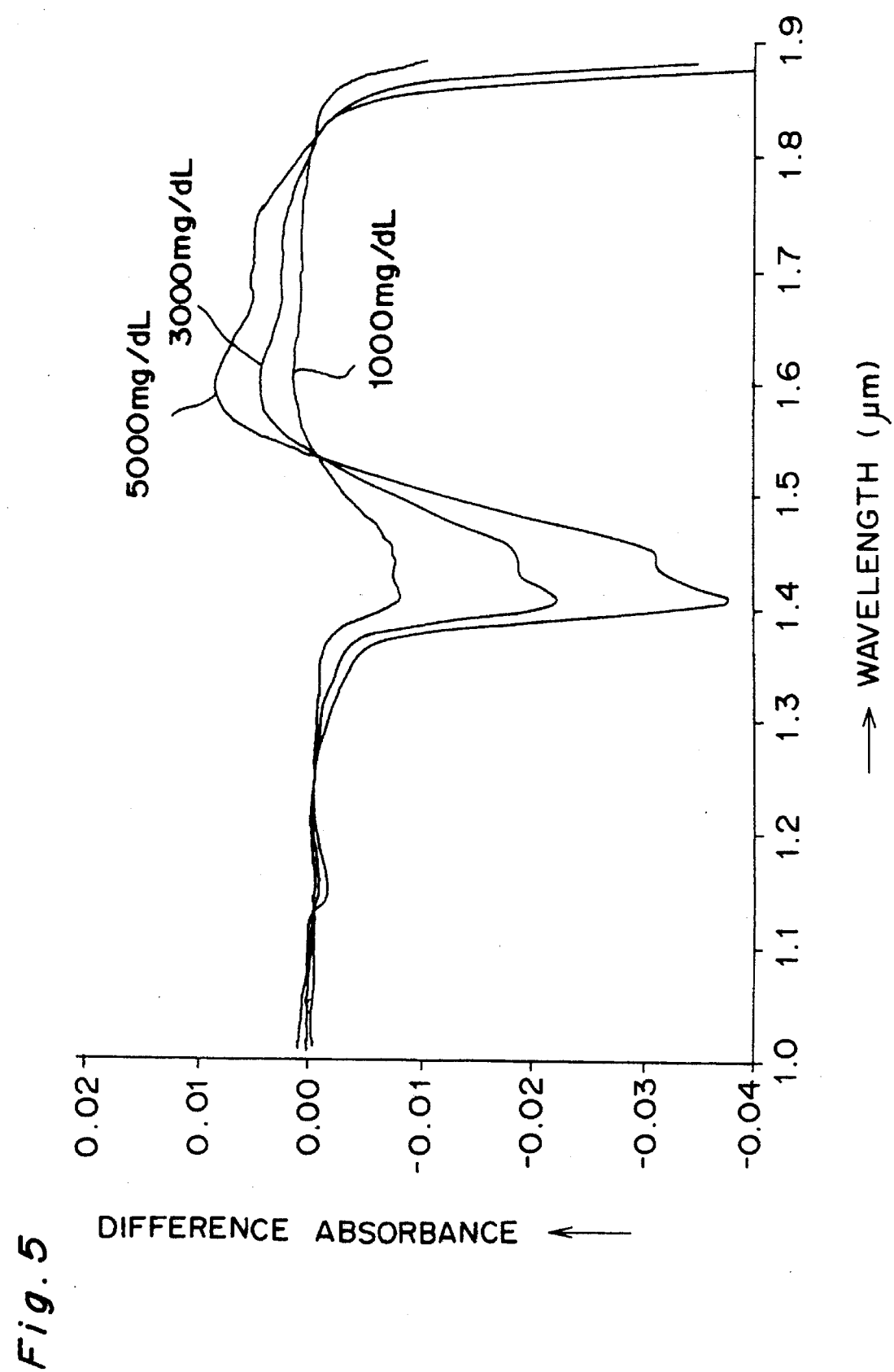
FIG. 5 shows the difference absorbance spectra with respect to standard pure water.

First, let us consider the glucose absorption band between the absorption peaks 1.43 μm and 1.93 μm of pure water. FIG. 3 shows the absorbance spectrum, and FIG. 4 shows its first derivative spectrum. Further, FIG. 5 shows the difference absorbance spectra. In the difference absorbance spectra of FIG. 5, the absorption by glucose is observed between 1.55 μm and 1.85 μm. Also, S-shaped characteristics are observed between 1.35 μm and 1.45 μm. These are due to the shift of the absorbance peak 1.43 μm of pure water caused by hydration. The central wavelength of the wavelength modulation can be chosen from the wavelength ranges, one between 1.45 μm and 1.58 μm, which is around the noninterference zero-crossing point, one between 1.6 μm and 1.67 μm, and one between 1.75 μm and 1.85 μm, which are less affected by interference and have steep slopes in an absorption band.

Figure 6:
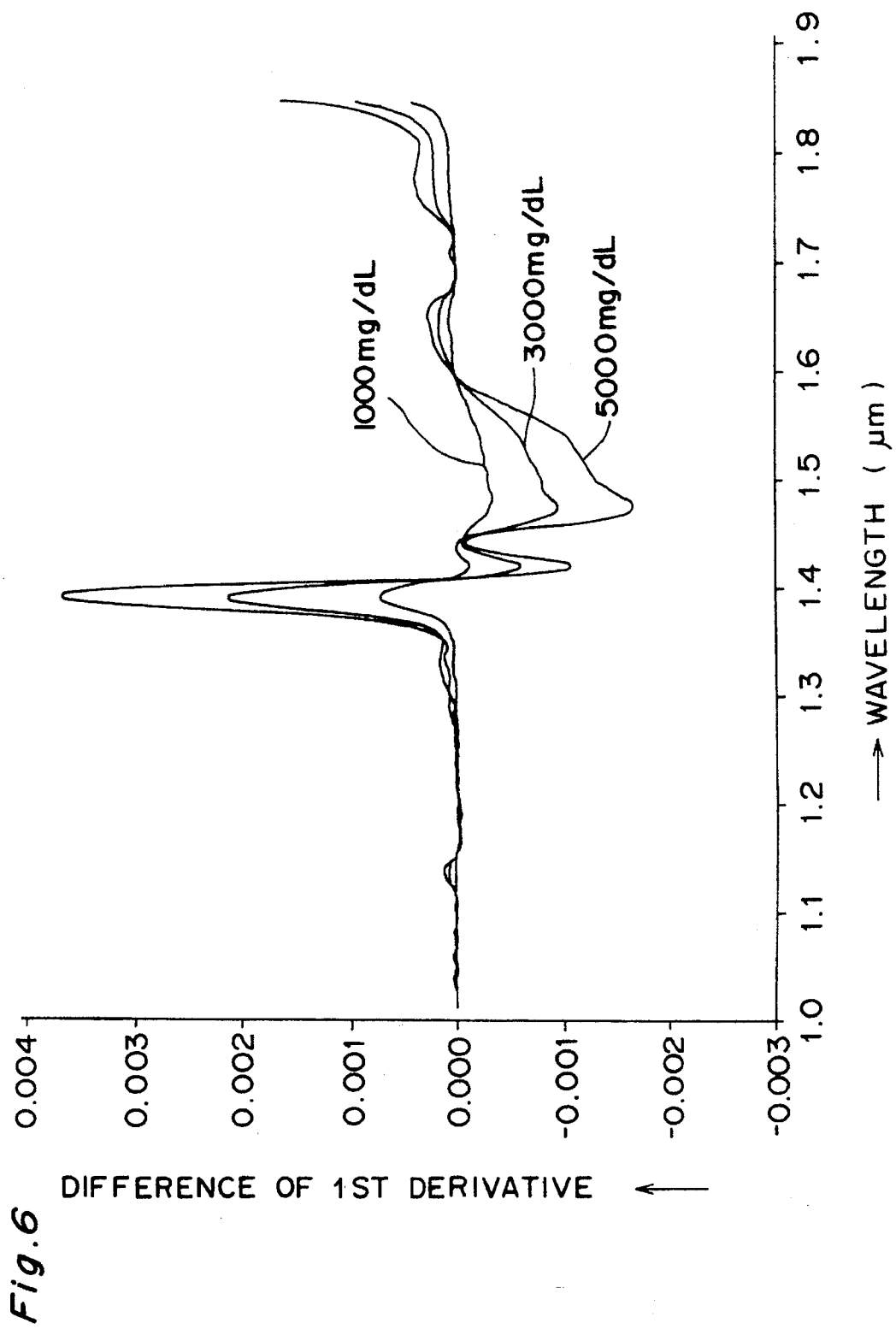
FIG. 6 shows the difference of the first derivative spectra.
Figure 10:
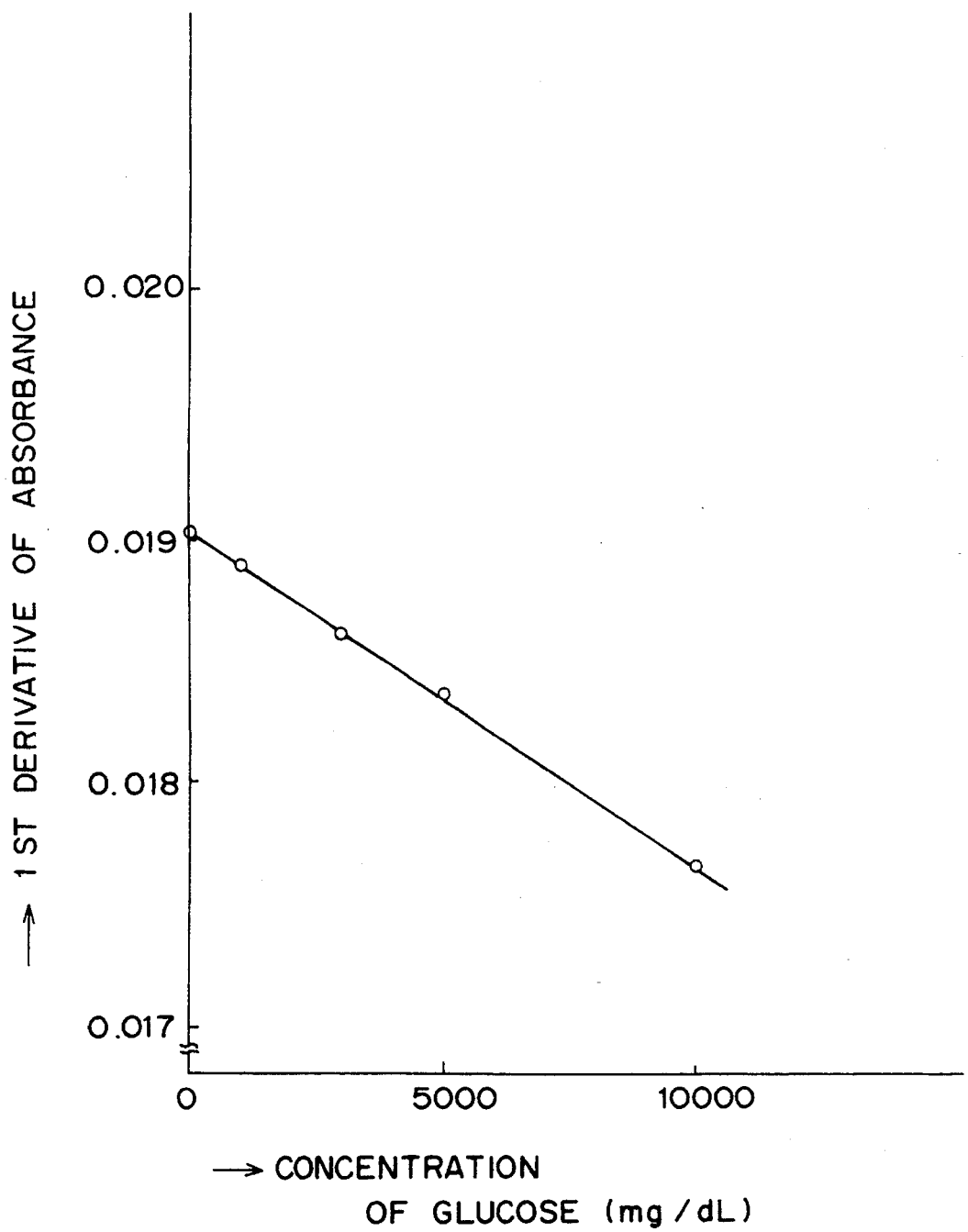
FIG. 10 shows the relationship between the concentration of glucose and the first derivative of an absorbance spectrum.

As is observed from the difference of the first derivative spectra shown in FIG. 6, it is clear that glucose can be determined by the first derivative spectrum. FIG. 10 shows the relationship between the first derivative of the absorbance and the glucose concentration at wavelength 1.555 μm.

Since wavelength-variable semiconductor lasers can be employed for the 1.5-μm band, the construction of the apparatus is easy. If wavelength-variable semiconductor lasers are applied to wavelength modulation, the characteristics of wavelength-variable semiconductor lasers can be effectively used to the maximum performance limit.

Figure 7:
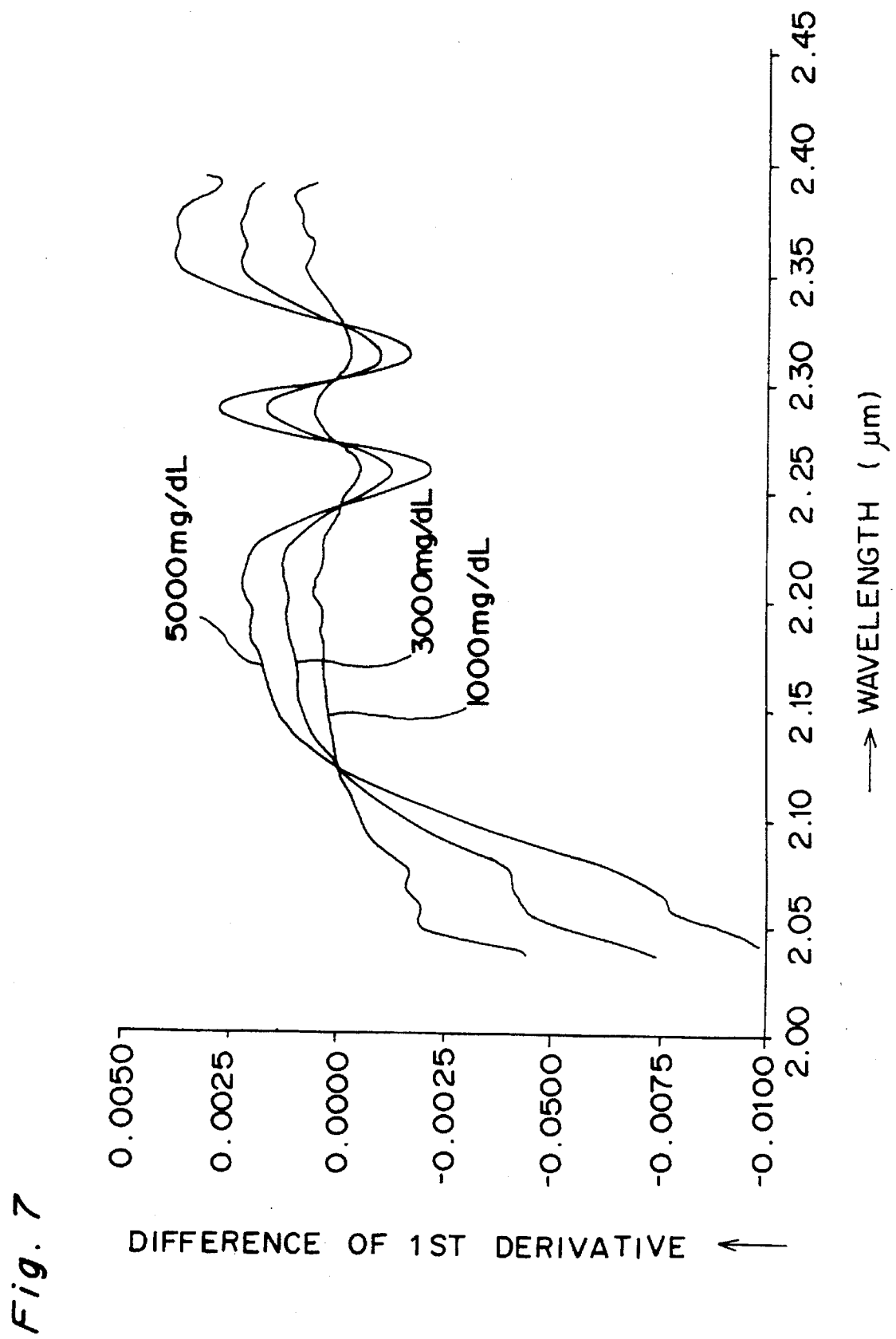
FIG. 7. shows the difference of the first derivative spectra.
Figure 8:
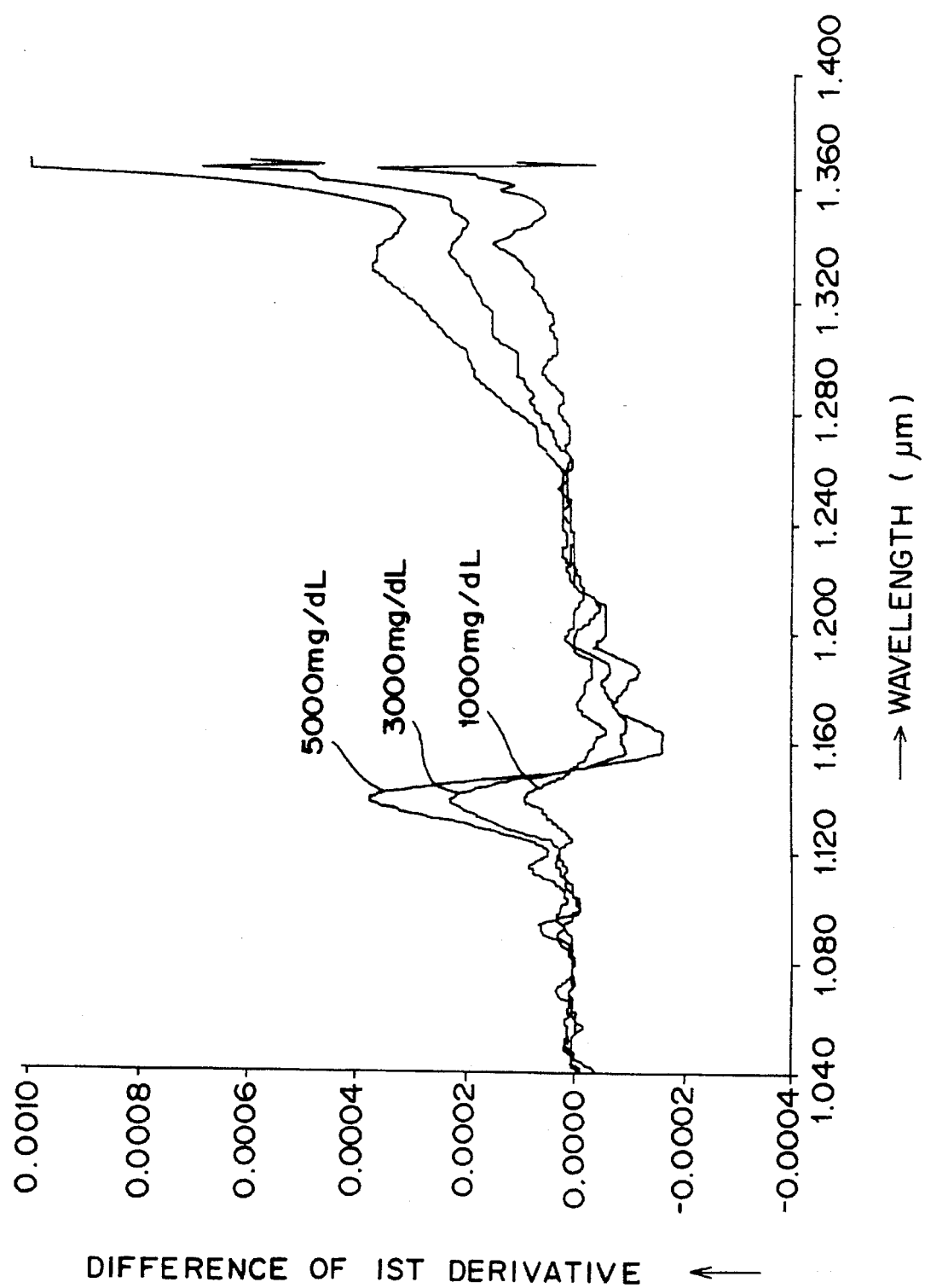
FIG. 8 shows the difference of the first derivative spectra.

Beyond the absorption peak 1.93 μm of pure water, there are absorption bands of glucose at 2.1 μm, 2.27 μm, and 2.33 μm. The slopes around these absorption peaks should be considered carefully. As is observed from the derivatives of difference absorbance spectra shown in FIG. 7, the central wavelength can also be chosen from 2.06~2.1 μm 2.1~2.24 μm 2.24~2.27 μm 2.27~2.3 μm 2.3~2.32 μm 2.32~2.38 μm Similarly, between the absorption peaks 0.96 μm and 1.15 μm of pure water, there is a broad absorption band of glucose at 1.06 μm. As is observed from the difference of the first derivative spectra shown in FIG. 8. The central wavelength can be chosen from the range between 1.07 μm and 1.25 μm and the range between 1.00 μm and 1.05 μm.

Figure 9:
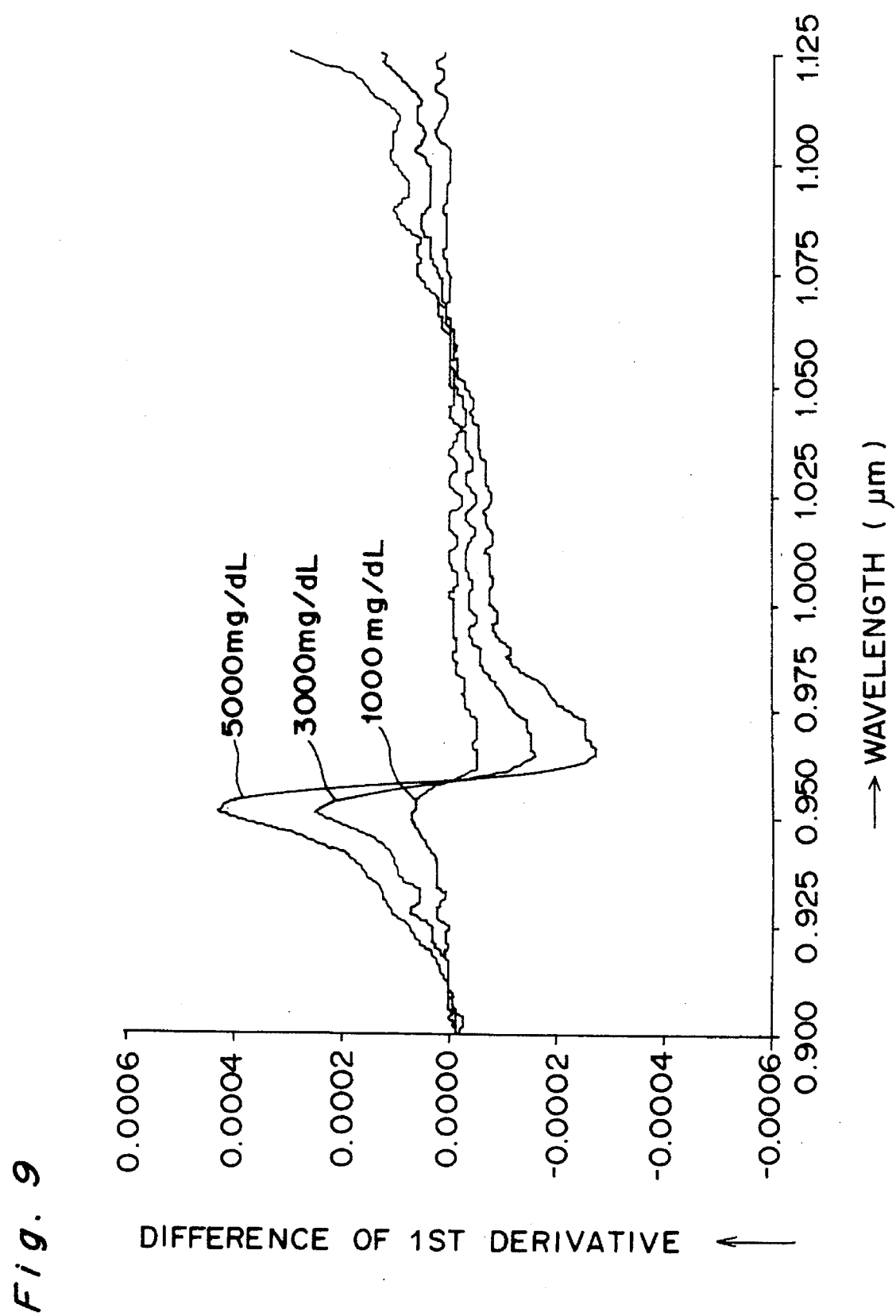
FIG. 9 shows the difference of the first derivative spectra.

Similarly, between the absorption peaks 1.15 μm and 1.43 μm of pure water, there is a broad absorption band of glucose at 1.25 μm. As is observed from the difference of the first derivative spectra shown in FIG. 9, the central wavelength can be chosen from the range between 1.28 μm and 1.36 μm and the range between 1.18 μm and 1.23 μm.

Figure 11:
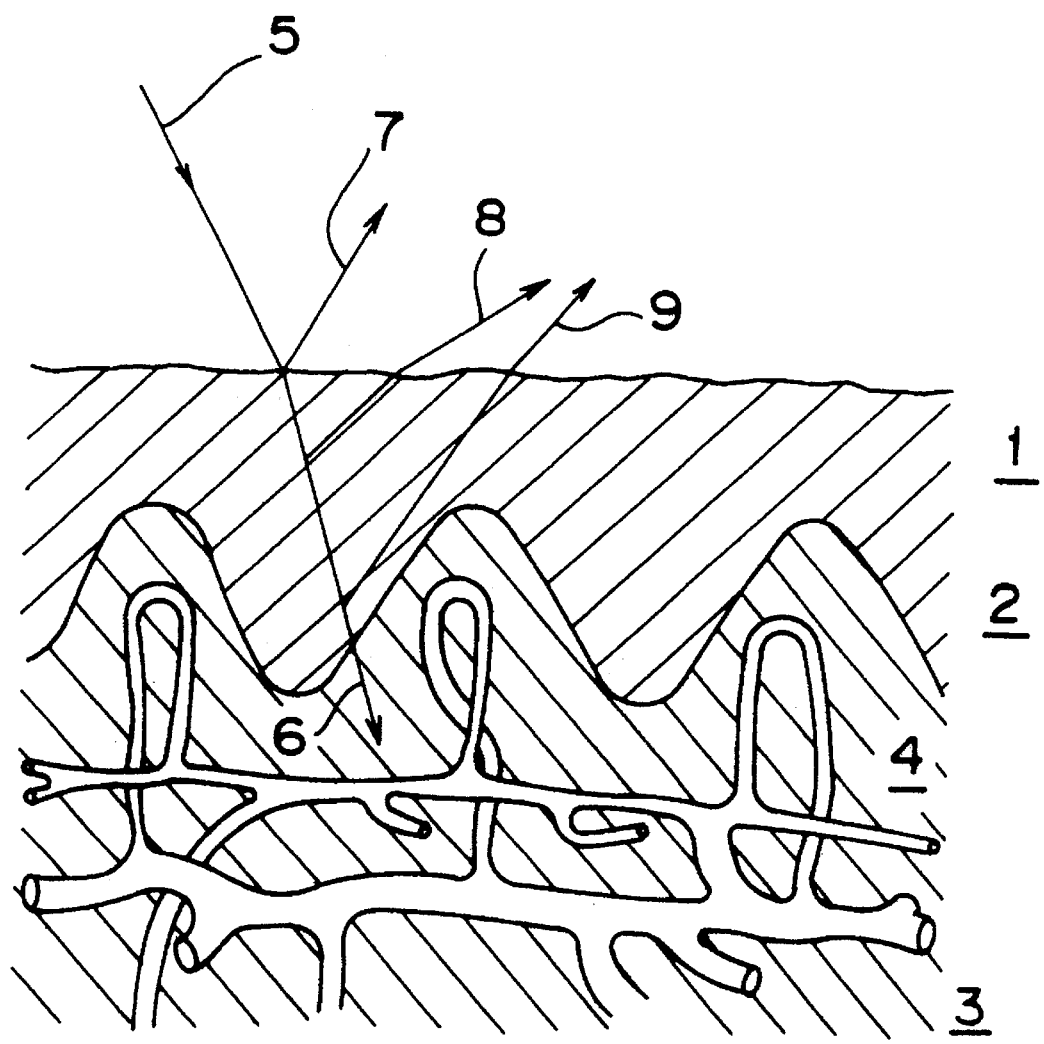
FIG. 11 shows the structure of human skin for describing its optical properties.

[4] Choice of optimal wavelength,

Human skin consists of the cornified layer 1, epidermis 2, and dermis 3 successively from the outside, as shown in FIG. 11, and has an anisotropic structure in the direction of depth. In measuring the concentration of glucose in the part in which body fluid containing blood components exists, i.e.—the capillary bed 4, by means of diffuse reflection through skin, the wavelength selection is important and inseparable from the method of measuring.

A longer-wavelength region near middle-infrared light and a shorter-wavelength region near visible light in the near-infrared region are compared in the following.

In the longer-wavelength region, light energy is absorbed strongly by water existing in the organism, so that it is hard to penetrate into a deeper part of the organism (skin). However, light is hard to be attenuated since it is less affected by scattering. Also, since the absorption coefficient of glucose in its existing absorption band is greater, the path length can be short, ie. the depth of light penetration can be relatively small.

In the shorter-wavelength region near visible light, light is less absorbed by water to reach a deep part of skin. However, light is easily affected and attenuated by scattering. Also, since the absorption coefficients of glucose in its absorption band are small, the path length must be large to raise the sensitivity of measurement.

In this way, there are various related factors for choosing optimal wavelength. In conclusion, an optimal wavelength for measurement of glucose is preferably chosen from the range between 1.45μ and 1.85 μm because of the chosen wavelength band described in [3] and the characteristic absorption coefficients of glucose, the depth of light penetrating skin, and a practical factor. The practical factor means the fact that a wavelength-variable semiconductor laser for coherent optical fiber communications can be employed.

[5] Diffuse reflectance spectra of skin and intensity-modulation spectroscopy

As described earlier, derivative data of high quality are obtained in real time by wavelength modulation without requiring computer processing. Derivative data are, in a way, data at one point, so that, from a practical standpoint, it is important that data are normalized and that various fluctuating factors such as changes in the temperature of the sample and interaction of chemical components are automatically compensated. The present invention combines wavelength modulation with intensity modulation to automatically compensate for these fluctuating factors.

A diffuse reflectance spectrum of skin is based on a signal obtained from the weak diffuse reflection of light which has been repeatedly absorbed and scattered inside skin and collected by an integrating sphere and detected by a detector. In relation to the anisotropic structure in the direction of depth, the diffuse reflectance spectrum is a mixture spectrum comprising the following spectral components of the incident light 5:

(a) Spectral components of regularly reflected light 7 on the surface of skin.

(b) Spectral components of diffuse-reflected light 8 from the cornified layer 1 or surface tissue that does not contain glucose.

(c) Spectral components of diffuse-reflected light 9 from the part 4 where body fluid containing blood components exist.

(d) Spectrum components of transmitted light through deeper tissue.

In general, the contribution of spectral components near the surface of skin is great, and the contribution of spectral components in part 4 where body fluid containing blood components exist is small. This fact characterizes an ordinary diffuse reflectance spectrum.

If we are concerned with the concentration of glucose in part 4 where body fluid containing blood components exists, and if we can determine and analyze a spectrum not containing the spectral components of the above (a) and (b), then clearly we can measure the concentration of glucose more accurately.

As a technique to realize this possibility, the inventors of the present application proposed a following technique of light-intensity modulation in Japanese Patent Application No. Sho-62-290821 and U.S. Pat. No. 4,883,953.

Figure 12:
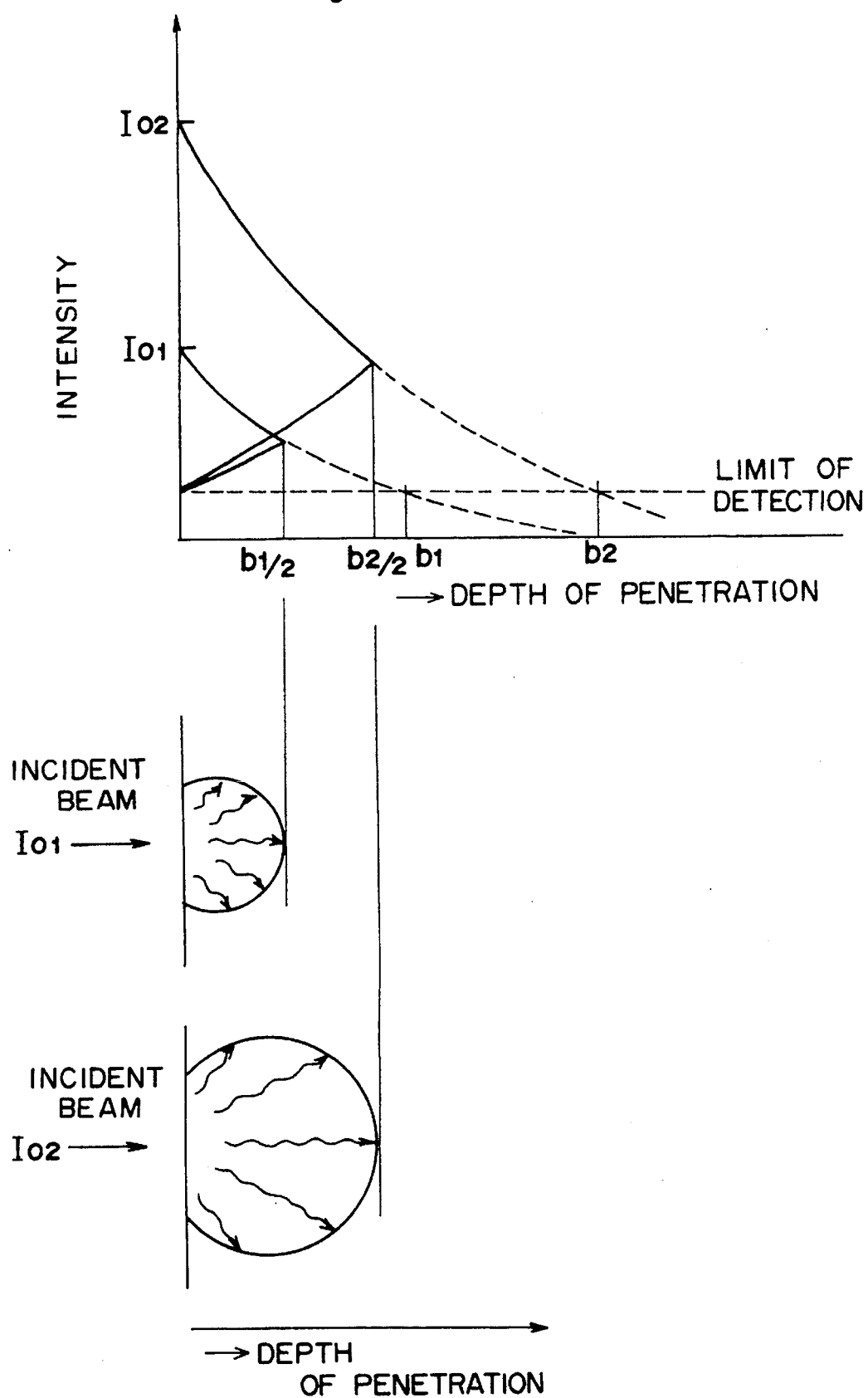
FIG. 12 shows a graph for describing the relationship between the intensity of incident light and the depth of light penetration.

The technique controls the depth of light penetration by varying the intensity of incident light. As shown in FIG. 12, when the intensity of incident light is great, then more information of greater depth is included than when the intensity is small. Therefore, the incident light of intensity $I_{01}$ at which penetration depth for a detection limit is $b_1$ is used, and the intensity $I_{s1}$ of diffuse-reflected light from depth $b_1/2$ is measured. Then the ratio between them is calculated by the following equation (3) for normalization.

$$A_1 = \log (I_{01}/I_{s1}) \quad (3)$$

$A_1$ has spectral information of only the part near the surface of skin.

Next, the incident light of intensity $I_{02}$ in which penetration depth for detection limit is $b_2$, which is greater than b2, is used, and the intensity $I_{s2}$ of diffuser-reflected light from depth $b_2/2$ is measured. Then the ratio between them is calculated by the following equation (4) for normalization.

$$A_2 = \log (I_{02}/I_{s2}) \quad (4)$$

$A_2$ contains spectral information of deeper part from the surface of skin. Then the difference $\Delta A$ between $A_1$ and $A_2$ is calculated.

$$\Delta A = A_2 - A_1 = \log (I_{02}/I_{s2}) - \log (I_{01}/I_{s1}) \quad (5)$$

The $\Delta A$ of the above equation (5) expresses spectral information from the baseline spectrum of an examined subject's tissue near the surface of the skin in which no glucose is contained. Therefore, $\Delta A$ is free from the influence of the subject's individual differences such as race, sex, and age.

The modulation of incident light can be performed by switching attenuators having different attenuation ratios by a rotating disk. The absorbances are normalized by calculating the above ratios (3) and (4) for each cycle of the modulation of the intensity of incident light, and the difference of the normalized absorbances is calculated by (5). Then the differences are accumulated and averaged for many cycles to improve the S/N ratio.

A regression equation is created using the averaged differences for samples having different concentrations of glucose and reference concentration values obtained by chemical analysis. Finally, using this regression equation, glucose of an unknown sample is determined.

We have described the algorithm of the technique of intensity modulation of incident light using the spectral intensity I. It is known by the method of regression that determinacy also exists between the derivative intensity and the concentrations. Therefore, in order to use the first derivative $D = \Delta A/\Delta \lambda$, we replace the absorbance A in equations (3), (4), and (5) with $\Delta A/\Delta \lambda$ to obtain the equations (8), (9), and (10) described later.

[6] apparatus for non-invasive measurement of blood sugar

Figure 13:
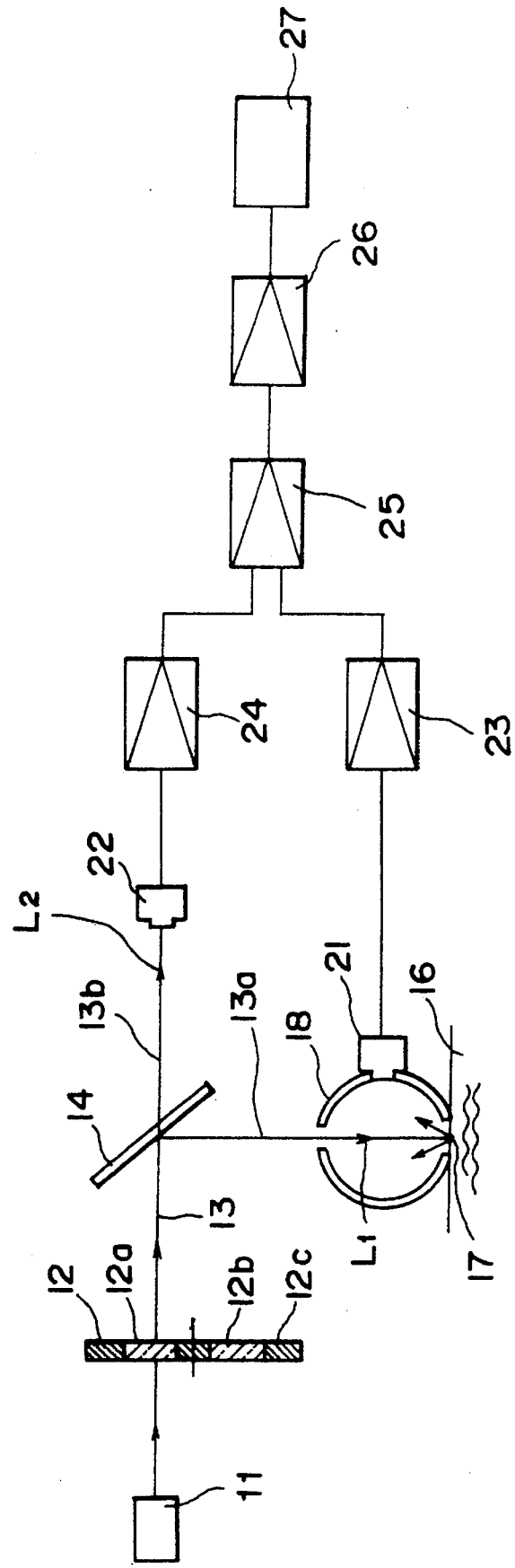
FIG. 13 shows a block diagram of an apparatus for non-invasive measurement of blood sugar.

FIG. 13 shows a block diagram of an apparatus for non-invasive measurement of blood sugar in accordance with the present invention.

The above apparatus for non-invasive measurement of blood sugar has as its components a wavelength-variable semiconductor laser 11, an attenuator 12 that periodically varies the intensity of wavelength-modulated laser light output from semiconductor laser 11, a beam splitter 14 that separates the optical path 13 of the wavelength-modulated and intensity-modulated light emitted from attenuator 12 into an optical path 13a and an optical path 13b, and an integrating sphere 18 that collects laser light transmitted or reflected after passing along optical path 13a and made incident on an examined portion 17 of skin 16 in which the blood sugar level is measured.

The above apparatus for non-invasive measurement of blood sugar levels also has as its components a first detector 21 that detects the intensity of the laser light collected by the integrating sphere 18, a second detector 22 that detects the intensity of laser light passing along optical path 13b, an amplifier 23 that amplifies the output of the first detector 21, an amplifier 24 that amplifies the output of the second detector 22, a logarithmic ratio amplifier 25 that outputs the logarithm of the ratio between the outputs of amplifiers 23 and 24, a lock-in amplifier 26 that detects the derivative spectral signal of a glucose absorbance spectrum in above examined portion 17 from the rate of change of the output of logarithmic ratio amplifier 25 with respect to a change in wavelength, an arithmetic processor 27 containing a microprocessor that calculates the blood sugar level in the above examined portion by processing a derivative spectral signal, which is a digital signal obtained by converting the above analog derivative spectral signal detected by the lock-in amplifier 26.

Laser light adjusted and controlled at the central wavelength $\lambda_i$ and the wavelength-modulation width $\Delta\lambda$ by wavelength-variable semiconductor laser 11 is separated into two beams by beam splitter 14 after being intensity-modulated by attenuator 12.

One laser beam $L_2$ passing through beam splitter 14 is converted into an electrical signal $I_0$ by second detector 22, so that the intensity of the incident light is monitored. The other laser beam $L_1$ is made incident on examined location 17 where the concentration of glucose is measured. The light diffuse-reflected from examined location 17 is converted into an electrical signal $I_s$ by the first detector 21 after being collected by integrating sphere 18.

The above electrical signals $I_s$ and $I_0$ are respectively amplified by the amplifiers 23 and 24, and is input to logarithmic ratio amplifier 25, which outputs the normalized absorbance signal expressed by the following equation (6).

$$A = \log(I_0/I_s) \tag{6}$$

Since the above electric signals $I_s$ and $I_0$ are values measured at the same time by the first detector 21 and the second detector 22 after the same laser light is separated by the beam splitter 14, the values of the above absorbance signal A are accurate and are hardly affected by drift.

Then only the amplitude of an alternating-current signal expressed by the following equation (7) is extracted by the lock-in amplifier 25.

$$D = \Delta A/\Delta\lambda \tag{7}$$

The alternating-current component is a signal proportionate to the slope of the spectrum of a sample at the central wavelength of the wavelength modulation.

As described earlier, the attenuator 12 varies the intensity of the incident light to vary the depth of light penetration into examined location 17 of skin 16 and switches two attenuator units 12a and 12b or more than those by a rotating disk 12c. The concentration of glucose in a part where body fluid containing blood components exists is measured accurately by the variation of the intensity of the incident light.

Lock-in amplifier 26 outputs an alternating-current signal expressed by the following equation (8) corresponding to the intensity $I_{01}$ of the incident light created by attenuator 12.

$$D_1 = \Delta A_1/\Delta\lambda \tag{8}$$

Lock-in amplifier 26 also outputs an alternating-current signal expressed by the following equation (9) corresponding to the intensity $I_{02}$ of the incident light created by attenuator 12.

$$D_2 = \Delta A_2/\Delta\lambda \tag{9}$$

Arithmetic processor 27 converts the above alternating-current signals $D_1$ and $D_2$ from analog to digital format and calculates the difference expressed by the following equation (10) for each cycle of the intensity modulation of the incident light.

$$\Delta D = D_2 - D_1 = \Delta A_2/\Delta\lambda - \Delta A_1/\Delta\lambda \tag{10}$$

Arithmetic processor 27 uses the values obtained by equation (10) and the data of a regression equation, which is obtained beforehand and not illustrated in FIG. 13, to determine the glucose concentration level in the examined location.

In the above determination of the glucose concentration level, if the processing of accumulation and averaging is performed for many cycles of the switching of attenuator units 12a and 12b of attenuator 12, then the S/N ratio is improved.

Further, if the incident light is intensity-modulated at more than 3 steps, then an optimal range of intensities of the incident light is found for the determination of the glucose concentration level, so that an optimal choice of attenuator 12 can be made, and the accuracy of the present technique is further enhanced. As a result, a standard diffuse plate used for calibration in prior diffuse reflectance methods becomes unnecessary.

Further, if light penetrating examined portion 17 does not leak from the bottom of the sample, ie. the condition of the so-called infinite thickness of the sample, is satisfied, then the information on the thickness of the examined location is not necessary unlike the transmission method.

Although the present invention has been fully described in connection with the preferred embodiments thereof with reference to the accompanying drawings, it is to be noted that various changes and modifications are apparent to those skilled in the art. Such changes and modifications are to be understood as being included within the scope of the present invention as defined by the appended claims unless they depart therefrom.

What is claimed is:

1. A method for non-invasive measurement of blood sugar levels comprising the steps of:

providing light which is intensity-modulated with a plurality of intensities as well as being wavelength-modulated;

applying the modulated light to an examined portion;

detecting an intensity of reflected light from said examined portion and an intensity of the incident light onto said examined portion for each intensity of said modulated light;

detecting the ratio of an intensity of said reflected light and said incident light;

detecting the rate of change in said ratio with respect to the change in wavelength due to the wavelength modulation;

extracting a derivative spectrum of an absorbance spectrum of glucose in said examined portion, and detecting the blood sugar level of said examined portion.

2. The method for non-invasive measurement of blood sugar levels as defined in claim 1, including extracting said derivative spectrum by accumulating and averaging in correspondence with the iteration of said wavelength modulation.

3. An apparatus for non-invasive measurement of blood sugar levels comprising:

a wavelength-modulated light generator for generating a wavelength-modulated light;

an intensity-modulator for intensity-modulating the wavelength-modulated light output from said wavelength-modulated light generator with a plurality of intensities;

a beam splitter for separating the optical path of the wavelength-modulated and intensity-modulated light emitted from said intensity modulator into two optical paths;

an optical collector for collecting the light passing along one of the two optical paths separated by said beam splitter, being incident on an examined location for assessing the blood sugar level, and being reflected therefrom;

a first optical detector for detecting an intensity of the light collected by said optical collector;

a second optical detector for detecting an intensity of the light passing along the other optical path separated by said beam splitter;

a ratio detector for detecting the ratio of the output of said first optical detector to the output of said second optical detector;

a derivative spectral signal detector for receiving a ratio signal from said ratio detector and for detecting the rate of change in said ratio signal with respect to the change in wavelength due to the wavelength modulation to detect a derivative spectral signal of an absorbance spectrum of glucose in said examined portion;

an arithmetic means for calculating the blood sugar level in said examined location based on the derivative spectral signal detected by said derivative spectral signal detector.

4. The apparatus for non-invasive measurement of blood sugar levels as defined in claim 3, wherein said wavelength-modulated light generator is a wavelength-variable semiconductor laser.

5. An apparatus for non-invasive measurement of blood sugar levels comprising:

a wavelength-variable light source for wavelength-modulated light;

an attenuator for periodically varying the intensity of the light output from the light source;

a beam splitter for separating light output from the attenuator into a reference light beam and a measuring light beam;

an integrating sphere for collecting light reflected from an examined portion of skin in which the blood sugar level is to be measured, the reflected light caused by the measuring light beam being projected on the examined portion of skin;

a first detector for detecting the intensity of the light collected by the integrating sphere;

a second detector for detecting the intensity of the reference light beam;

first and second amplifiers for respectively amplifying outputs of said first and second detectors;

a logarithmic ratio amplifier for receiving outputs from said first and second amplifiers and for outputting a logarithm of a ratio between outputs of the first and second amplifiers;

a lock-in amplifier for receiving an output from said logarithmic ratio amplifier and for detecting a derivative spectral signal of a glucose absorbance spectrum for the examined portion from a rate of change of the output of the logarithmic ratio amplifier with respect to a change in wavelength;

a processing means for receiving an output from said lock-in amplifier and for calculating a blood sugar level in the examined portion by processing the derivative spectral signal detected by said lock-in amplifier.

* * * * *